United States Patent [19]
Shido

[11] Patent Number: 6,108,073
[45] Date of Patent: Aug. 22, 2000

[54] ELECTROMAGNETIC WAVE DETECTING SYSTEM

[75] Inventor: Mahito Shido, Yokohama, Japan

[73] Assignee: Kabushiki Kaisha Toshiba, Kawasaki, Japan

[21] Appl. No.: 09/015,524

[22] Filed: Jan. 29, 1998

[30] Foreign Application Priority Data

Jan. 29, 1997 [JP] Japan ..................................... 9-015293

[51] Int. Cl.$^7$ .................................................. G01N 21/00
[52] U.S. Cl. ............................................. 356/72; 324/73.1
[58] Field of Search ................................ 356/72, 39, 411; 250/458.1, 374, 338.1; 324/73.1, 642

[56] References Cited

U.S. PATENT DOCUMENTS

| | | | |
|---|---|---|---|
| 5,196,786 | 3/1993 | Usami et al. ........................... | 324/73.1 |
| 5,463,226 | 10/1995 | Matsuzaki et al. ................... | 250/336.1 |
| 5,682,038 | 10/1997 | Hoffman .................................... | 356/39 |

*Primary Examiner*—Frank G. Font
*Assistant Examiner*—Tu T. Nguyen
*Attorney, Agent, or Firm*—Foley & Lardner

[57] ABSTRACT

An electromagnetic wave detecting system free from restriction of shutter speed has a detector for detecting an electromagnetic wave having a specified wavelength generated from a device under test, a controller for outputting a drive signal for driving the device under test, for effecting the detector to detect an electromagnetic wave from the device under test for a first time interval from a predetermined time point to a detection start point during a first period to obtain a first detected value, and for effecting said detector to detect an electromagnetic wave from the device under test for a second time interval from the predetermined time point to a detection end point during a second period to obtain a second detected value, a first memory device for storing the first detected value, a second memory device for storing the second detected value, and a subtracter device for obtaining a third detected value which corresponds to a period from the detection start point to the detection end point by performing subtraction of the first detected value and the second detected value.

13 Claims, 4 Drawing Sheets

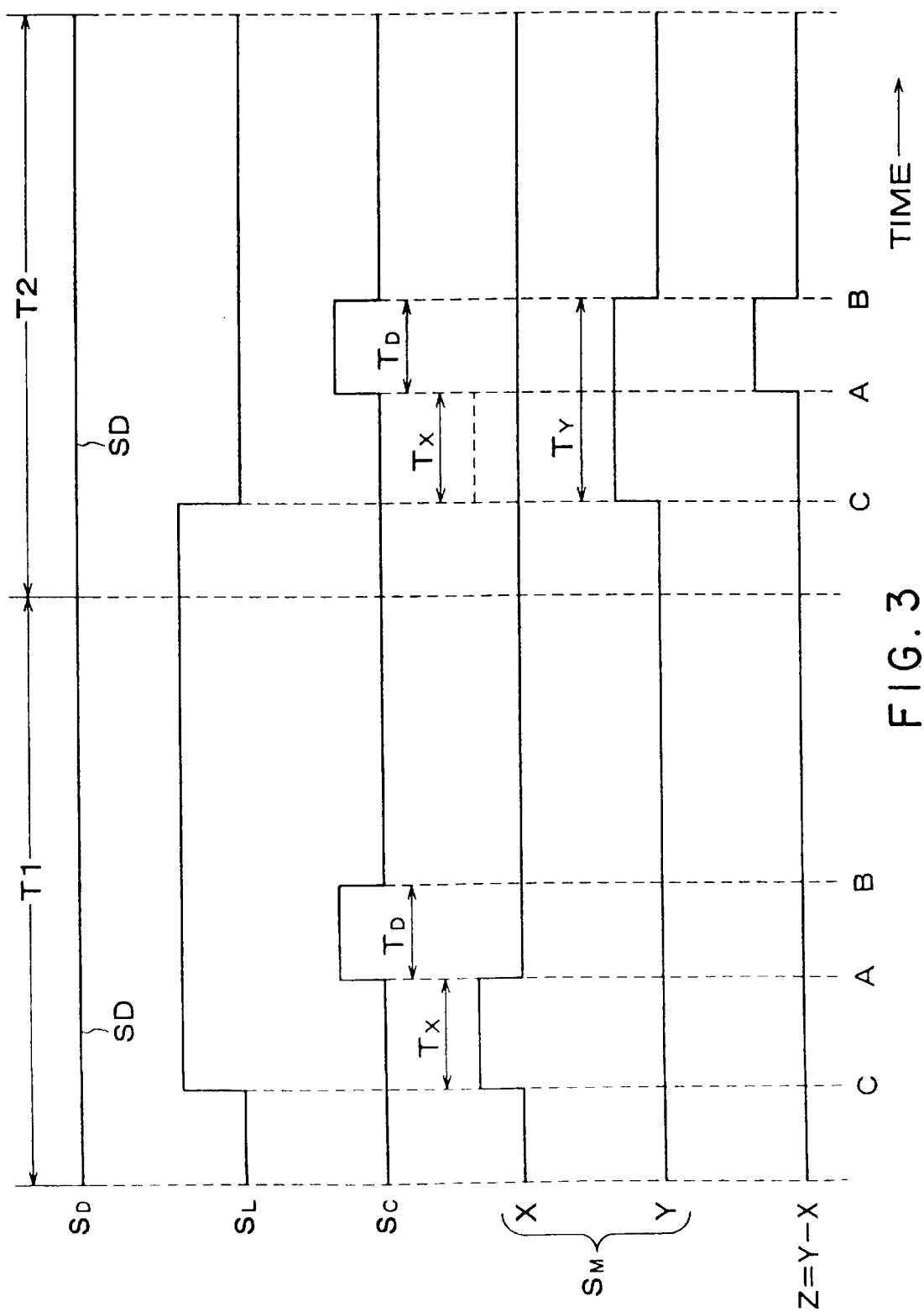

X

Y

Y−X

ELECTROMAGNETIC WAVE DETECTING SYSTEM

BACKGROUND OF THE INVENTION

This invention relates to an electromagnetic wave detecting system which detects electromagnetic waves having specific wavelengths, and especially to an electomagnetic wave detecting camera system which is preferably suited to identify locations where hot electrons are generated and locations where resistive current leaks are generated.

For such type of prior art electromagnetic wave detecting system, there has been used an emission microscope or a microscope, which detect only electromagnetic waves having specific wavelengths.

In a case of detection using an infrared microscope, a semiconductor device as a device under test (DUT) is placed directly under the infrared microscope and as well a desired driving voltage is applied to the semiconductor device. Then, images of the semiconductor device at specified timings are taken by a high sensitive camera and recorded in a memory provided in a system controller, etc. By synthesizing such images, hot electron generating points and/or resistive current leaking points are identified.

In such analysis using the high sensitive camera, it is necessary to appropriately control open/close of a shutter of the camera at a specified timing during operation of the semiconductor device, and/or to control start and end of taking detected signals in the system.

With recent increase of the operating frequency of semiconductor devices, a strong demand exists for shortening detection time according to kinds of electromagnetic wave to be detected. However, since a shutter has a mechanical structure, its open/close operation does not follow its open/close control signal when a pulse width of the open/close control signal is narrowed. Therefore, there is a lower limit in the pulse widths of the shutter open/close control signal, and as a result, decreasing detection time under the limit is impossible to decrease the pulse width under the limit value. As a result, there is a problem that the detection time is hardly shortened.

SUMMARY OF THE INVENTION

Therefore, it is an object of the present invention to provide an electromagnetic wave detecting system which enables observation in narrower period than the low limit pulse width of shutter open/close control signal.

According to the present invention, there is provided an electromagnetic wave detecting system comprising:

a detector for detecting electromagnetic wave having a specified wavelength generated from a device under test;

a controller for outputting a drive signal for driving the device under test, for effecting said detector to detect electromagnetic wave from the device under test for a first period from a predetermined time point to a detection start point during a first period to obtain a first detected value, and for effecting said detector to detect electromagnetic wave from the device under test for second interval from the device under test for a second period from the predetermined time point to a detection end point during a second period to obtain a second detected value;

a first memory device for storing said first detected value, a second memory device for storing said second detected value; and a subtractor for obtaining a third detected value which corresponds to a period from the detection start point to the detection end point by performing subtraction of said first detected value and said second detected value.

In this electromagnetic wave detecting system, since a detected value is obtained by subtracting a first detected value obtained from a predetermined timing to a start point of detection from a second detected value obtained from the predetermined timing to an end point of the detection, there is no restriction by shutter operation and detection in short time can be possible.

BRIEF DESCRIPTION OF THE DRAWINGS

In the attached drawings,

FIG. 3 is a timing chart explaining an operation of the embodiment showing in FIG. 1, FIGS. 4A–4C are schematic diagrams showing a procedure of obtaining detected value according to the present invention.

DESCRIPTION OF THE PREFERRED EMBODIMENT

A preferred embodiment of the present invention will be explained with reference of the attached drawings.

Figure 1:
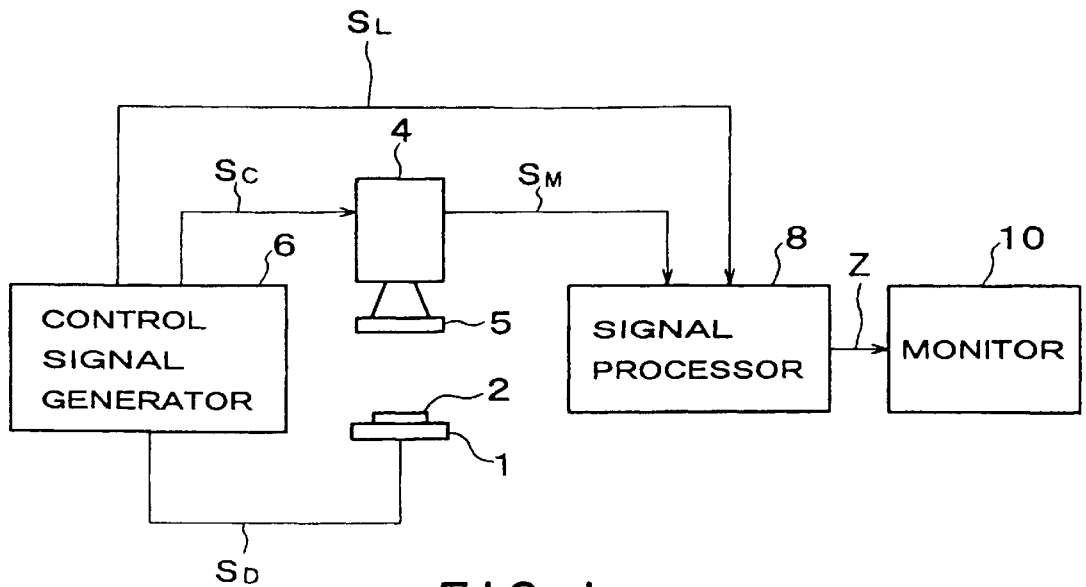
FIG. 1 is a block diagram showing an embodiment of an electromagnetic wave detecting system according to the present invention.

FIG. 1 is a block diagram showing an embodiment of an electromagnetic wave detecting system according to the present invention. A semiconductor device 2 as a device under test (DUT) is supported on a movable table 1. A camera 4 for observing the external view of the DUT is provided above the movable table 1. In the front of a lens of the camera, a stop and a filter 5 are provided. The filter has preferably a specific characteristics having high sensitivity for an electromagnetic wave of specified wavelength, for example, longer wavelength than the ordinary visible light, or high transparency for an electromagnetic wave of specified wavelength.

An optical microscope may be disposed between the camera 4 and the DUT 2, and images of the microscope may be taken by the camera 4. Such function of the microscope may be provided in the camera 4.

The semiconductor device 2 is driven by a driving signal $S_D$ having predetermined sequence and repeating for period T, which has been generated by a control signal generator 6.

For the camera 4, a control signal $S_C$ for opening/closing the shutter thereof, which is in synchronism with the signal $S_D$, is supplied from the control signal generator 6.

A detected amount signal $S_M$ expressing detected amount of electromagnetic wave of a specified wavelength is output from the camera 4 and supplied to a signal processor 8. As will be mentioned later, in this embodiment, since signal data are obtained for two periods, a signal $S_L$ for designating either one of the two periods is output from the control signal generator 6 and supplied to a signal processor 8.

The control signal generator 6 includes a microprocessor (not shown) for generating the abovementioned signals.

A monitor 10 for displaying processed results is also connected to the signal processor 8.

Figure 2:
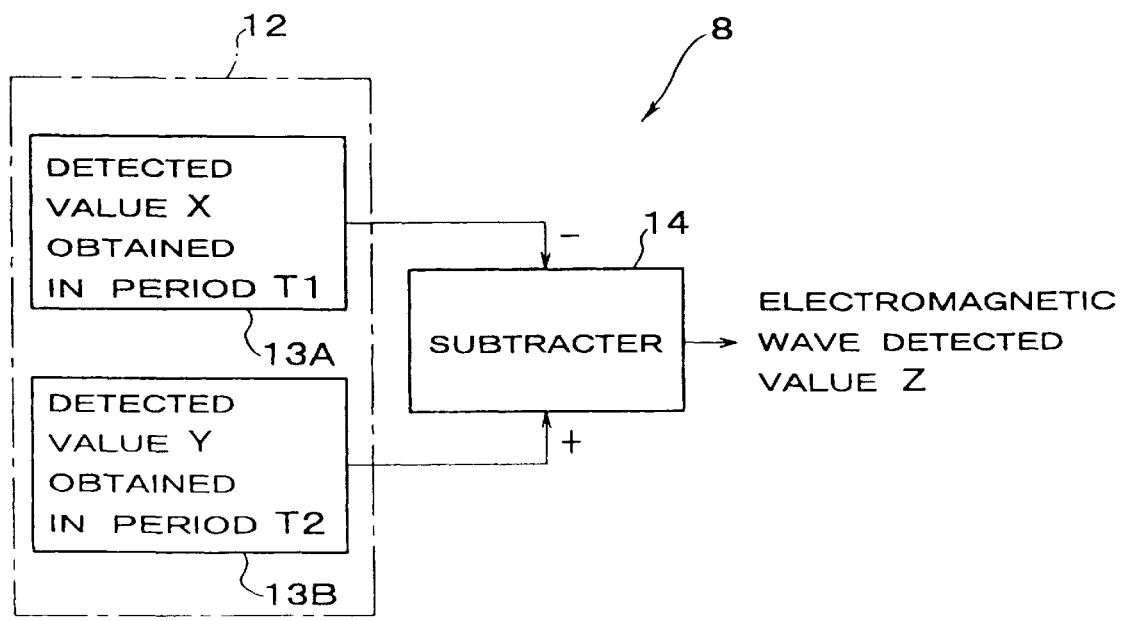
FIG. 2 is a block diagram showing detailed construction of the embodiment shown in FIG. 1.

FIG. 2 is a block diagram showing a detailed construction of the signal processor 8. This signal processor 8 has a memory device 12 which has a first memory area 13A where a detection value X obtained during the first period Ti and a second memory area 13B where a detection value Y obtained during the second period T2 and a subtracter 14 which computes the difference between the stored data X and Y and outputs the difference.

Now, the operation of this embodiment will be described with reference to FIGS. 3–5. In the following description, it is assumed that the identical drive pulses $S_D$ are supplied to the DUT and the identical control signals SC are supplied to the camera 4 in two consecutive periods.

In the first period T1, a signal $S_L$ rises at a time C which is a start point of detection by the camera 4. This signal expresses that electromagnetic wave is detected from the rise of $S_L$ (point C) to the rise of the control signal $S_C$ (point A) and a value X for a period $T_X$ as the electromagnetic wave detection signal $S_M$. This value X is stored in the first memory area 13A of the memory unit 12.

Then, in the second period TZ, the signal $S_L$ falls at the time of start point C of detection by the camera. This signal expresses that electromagnetic wave is detected from the fall of $S_L$ (point C) to the fall of the control signal $S_C$ (point B). As a result, a value Y for a period $T_Y$ as the electromagnetic wave detection signal $S_M$. This value Y is stored in the second memory area 13B of the memory unit 12.

For these detected values X and Y stored in the memory areas 13A and 13B, a difference thereof is calculated by a differential processor 14 and detected electromagnetic wave value Z=Y−X is output.

Figure 4A:
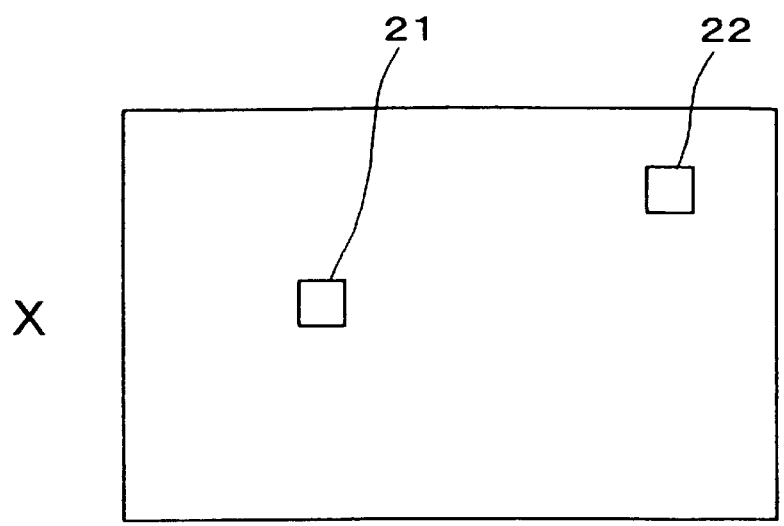
Figure 4B:
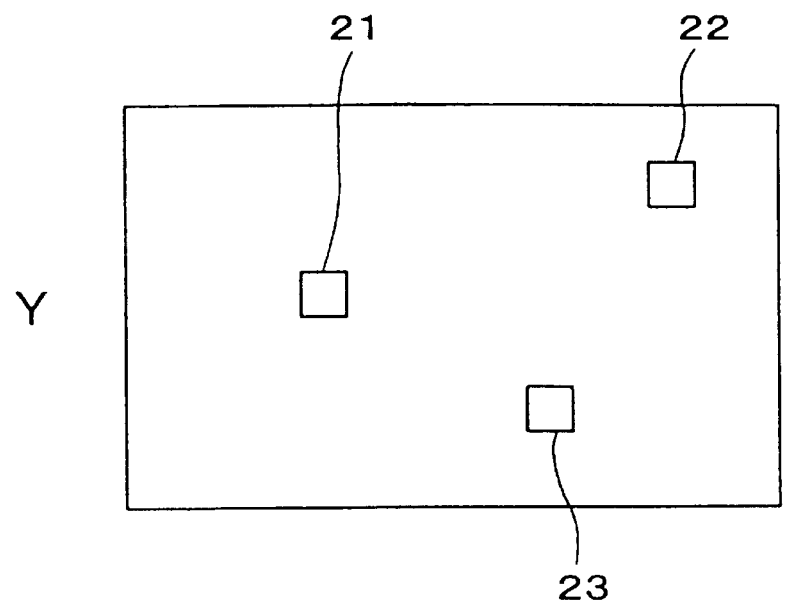
Figure 4C:
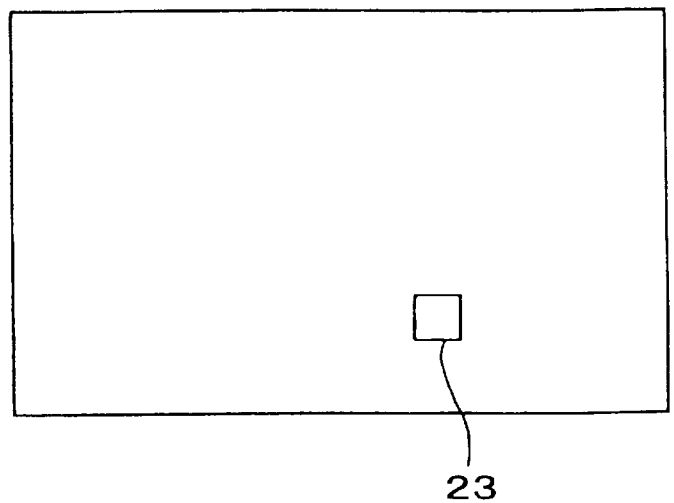

FIGS. 4A and 4D are schematic diagrams showing a procedure of obtaining detected value. FIG. 4A is an image corresponding to the detected value X obtained in the period T1, lightened portions 21 and 22 are observed. FIG. 4B is an image corresponding to the detected value Y obtained in the period T2, lightened portions 21, 22 and further 23 are observed. FIG. 4C is an image corresponding to the detected value Z=Y−X obtained by the subtracter 14. In FIG. 4C, only the portion 23 is lightened, and therefore, it is understood that there has been some change in the portion.

It should be noted that the function of the subtracter 14 can be obtained by software implemented in a microprocessor.

By superimposing the image on a microscopic image which has previously obtained on a display of the monitor 10, locations where hot electrons are generated and locations where resistive current leak is generated are easily identified.

Figure 5:
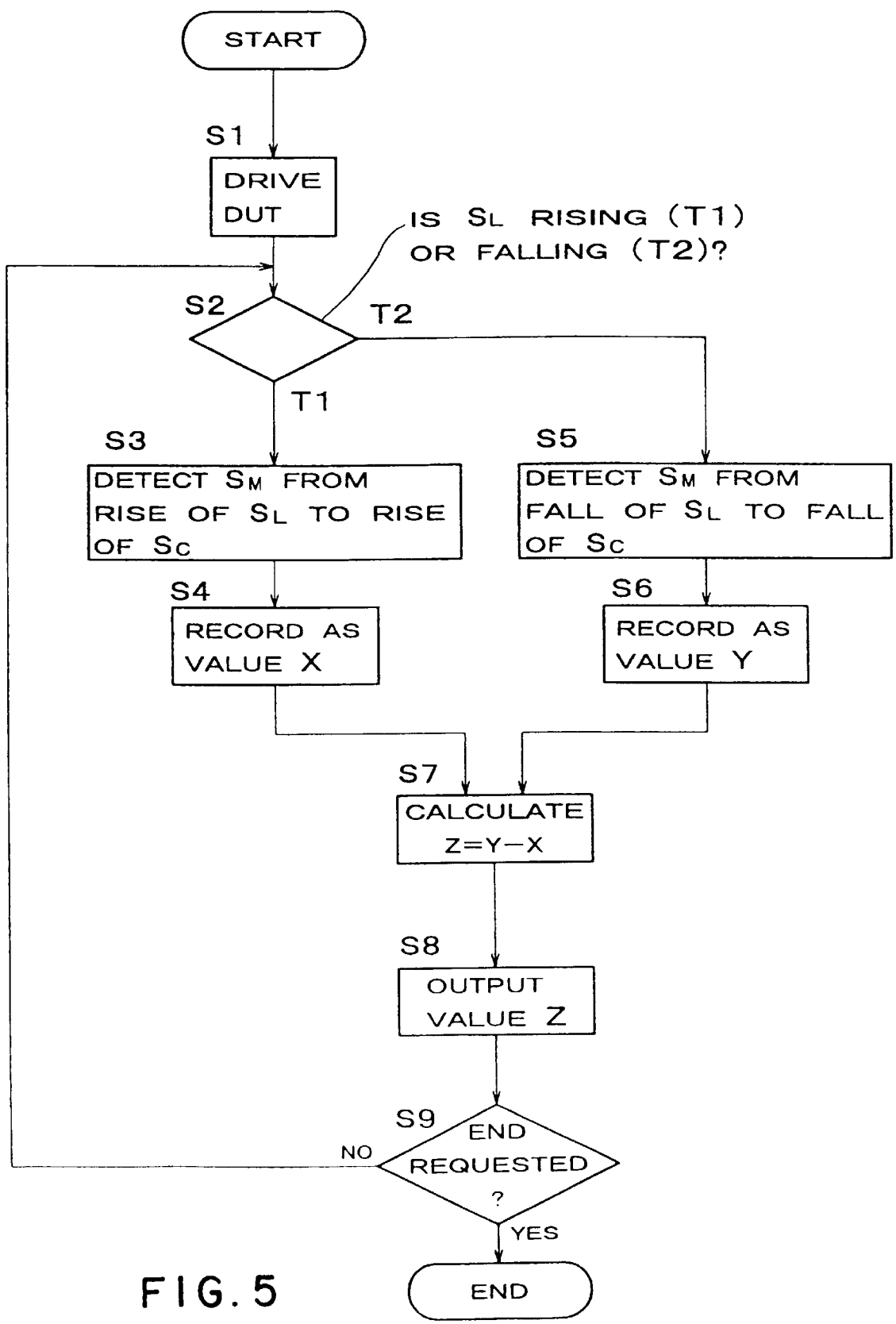
FIG. 5 is a flowchart showing an operation of the embodiment shown in FIG. 1.

FIG. 5 shows a flowchart showing the abovementioned whole operations.

First, a drive signal SD generated by the control signal generator 6 is supplied to the DUT 2, and the DUT is driven by a predetermined sequence (step S1). At that time, the control signal generator 6 also outputs the control signal $S_C$ for the camera 4 and the signal $S_L$ for determining periods.

In the next step, it is judged if the signal $S_L$ rises or falls (step S2). When the signal $S_L$ rises, the period now is determined as period T1, and the value $S_M$ from the rise of $S_L$ to the rise of the control signal $S_C$ is detected (step S3). This value is stored as value X in the first memory area 13A in the memory 12 (step 54).

On the other hand, when the signal SL falls, the period now is determined as period T2, and the value $S_M$ from the fall of $S_L$ to the fall of the control signal $S_C$ is detected (step S5). This value is stored as value Y in the second memory area 13B in the memory 12 (step S6).

Next, the detected value Z=Y−X corresponding to the control signal $S_C$ is obtained by subtracting the value X from the value Y in the subtracter 14 (step S7). This value Z is output (step 88) and displayed on a screen of the monitor 10.

These series of operation is repeated unless an end instruction is applied.

Thus, in the two kinds of periods discriminated by the signal $S_L$, the detection start timings of the camera are the same, but the detection end timings of the camera are different from each other for the desired detection time. And a detected value corresponding to the real detecting time is obtained as a subtraction signal, so that no restriction 6 caused by shutter speed which often appeared in the conventional analyzer. The reason will be described in detail.

In the conventional apparatus, since a detected value has been directly obtained from the detection start point A to the detection end point B using the control signal $S_C$, that there is a lower limit value in narrowing the pulse width $T_D$.

In contrast, according to the present invention, direct detection using the pulse width $T_D$ is not employed. Instead, two detected values are obtained from a time point C prior to the detection start timing A to a rise point and a fall point of the control signal, respectively and the desired detected value is obtained by the subtraction of these values. Therefore, the detection does not bear the restriction of the open/close speed of the shutter, and good resolution of hundreds of picoseconds can be obtained, though it depends the performance of the pulse generator.

In the above-mentioned embodiment, the detection start points are the same for two periods and detection end points are different. However, it may be possible to employ the same detection end point and different detection start points.

Furthermore, in the above-mentioned embodiment, two consecutive periods are employed, however, an averaging in which detected values of a plurality of periods (same number for both periods) are accumulated can be employed to reduce the dispersion and to increase the s/n ratio.

Still further, though the DUT is a finished semiconductor device in the above-mentioned embodiment, the present invention is not limited to this, and the invention can be applied to an water just completed its wafer process, a printed circuit board on which semiconductor devices are mounted, etc. Also, items to be analyzed are not limited to the hot electron generating point or resistive current leak point.

What is claimed is:

1. An electromagnetic wave detecting system comprising:
   a drive signal generator coupled to a device under test for outputting a drive signal to drive said device under test;
   a detector for detecting an electromagnetic wave having a specified wavelength generated from the device under test when it is driven by said drive signal;
   a controller for effecting said detector to detect the electromagnetic wave amount from the device under test for a first time interval from a predetermined time point to a detection start point during a first period to obtain a first detected value, and for effecting said detector to detect the electromagnetic wave amount from the device under test for a second time interval from the predetermined time point to a detection end point during a second period to obtain a second detected value;
   a first memory for storing said first detected value;
   a second memory for storing said second detected value; and a subtracting device for obtaining a third detected value which corresponds to a period from the detection start point to the detection end point by performing subtraction of said first detected value and said second detected value.

2. The electromagnetic wave detecting system according to claim 1, wherein the detector is a camera.

3. The electromagnetic wave detecting system according to claim 2, wherein the camera obtains image of the device under test through a filter having high sensitivity for longer wavelength wave than visible light.

4. The electromagnetic wave detecting system according to claim 2, wherein the camera obtains image of the device under test through a filter having high sensitivity for shorter wavelength wave than visible light.

5. The electromagnetic wave detecting system according to claim 1, further comprising a displaying device for visibly displaying said third detected value.

6. The electromagnetic wave detecting system according to claim 1, wherein said predetermined time point is a time point prior to the detection start point.

7. The electromagnetic wave detecting system according to claim 1, wherein said predetermined time point is a time point followed to the detection end point.

8. The electromagnetic wave detecting system according to claim 1, wherein said first and second detected values are accumulated value for a plurality of periods.

9. The electromagnetic wave detecting system according to claim 1, wherein said electromagnetic wave has shorter wave length than visible light.

10. The electromagnetic wave detecting system according to claim 1, wherein said electromagnetic wave has longer wave length than visible light.

11. An electromagnetic wave detecting system comprising:

a detector for detecting an electromagnetic wave having a specified wavelength generated from a device under test;

a controller in communication with the device under test for outputting a drive signal for driving the device under test, the controller in communication with said detector for effecting said detector to detect the electromagnetic wave amount from the device under test for a first time interval from a predetermined time point to a detection start point during a first period to obtain a first detected value and for effecting said detector to detect the electromagnetic wave amount from the device under test for a second time interval from the predetermined time point to a detection end point during a second period to obtain a second detected value;

a first memory device for storing said first detected value;

a second memory device for storing said second detected value; and a subtracting device for obtaining a third detected value which corresponds to a period from the detection start point to the detection end point by performing subtraction of said first detected value and said second detected value;

wherein said first and second detected values are an accumulated value for a plurality of periods.

12. A method for detecting an electromagnetic wave, comprising:

outputting a drive signal to drive a device under test ("DUT");

detecting an electromagnetic wave having a specified wavelength generated from the DUT when it is driven by said drive signal;

controlling a detector to detect an electromagnetic wave amount from the DUT for a first time interval from a predetermined time point to a detection start point during a first period to obtain a first detected value, and detecting the electromagnetic wave amount from the DUT for a second time interval from the predetermined time point to a detection end point during a second period to obtain a second detected value;

storing said first detected value;

storing said second detected value; and obtaining a third detected value which corresponds to a period from the detection start point to the detection end point by subtraction of said first detected value and said second detected value.

13. The method of claim 12, wherein said first and second periods are consecutive in time.

* * * * *